United States Patent [19]

Unger

[11] Patent Number: 4,872,552

[45] Date of Patent: Oct. 10, 1989

[54] SAFETY PACKAGING FOR HYPODERMIC SYRINGES WITH NEEDLES AND THE LIKE

[75] Inventor: Larry E. Unger, Gadsden, Ala.

[73] Assignee: Mid-South Products Engineering, Inc., Gadsden, Ala.

[21] Appl. No.: 271,873

[22] Filed: Nov. 16, 1988

[51] Int. Cl.[4] .......................... A61M 5/00; A61M 5/32
[52] U.S. Cl. .................................. 206/365; 604/110; 604/198; 604/263; 604/192; 604/51
[58] Field of Search ................ 206/365; 604/110, 197, 604/198, 263, 192, 51

[56] References Cited

U.S. PATENT DOCUMENTS

| | | | |
|---|---|---|---|
| 2,836,942 | 6/1958 | Miskel | 206/365 |
| 3,828,775 | 8/1974 | Armel | 206/365 X |
| 4,634,428 | 1/1987 | Cuu | 206/365 X |
| 4,643,722 | 2/1987 | Smith, Jr. | 206/365 X |
| 4,664,259 | 5/1987 | Landis | 206/365 |
| 4,728,320 | 3/1988 | Chen | 604/110 |
| 4,728,321 | 3/1988 | Chen | 604/110 |
| 4,735,311 | 4/1988 | Lowe et al. | 206/365 |

*Primary Examiner*—William Price
*Attorney, Agent, or Firm*—Donald W. Phillion

[57] ABSTRACT

A safety package (54) for preventing accidental skin pricking by a hypodermic syringe type needle (16) having a needle hub (14) joining the needle (16) to the syringe (18) and comprising a first tubular section (12) securable at its first end to the needle hub (14). A second tubular section (54) is secured at a first end to a hinge (56) and surrounds the needle (16) in a first position (FIG. 1) with a longitudinal slot (58) formed therein and positioned to pivot about the hinge (56) and away from the needle (16) to a second position (FIG. 2) with the needle (16) passing through the longitudinal slot (58, FIG. 3) to expose the needle (16) for use and, after use of the needle, to pivot the second tubular section (54) back to its first position. The second tubular section is axially connected to the first tubular section (12) and has its second end extending beyond the needle point and containing therein a non-attached, movable element (19) therein which is positioned to allow the second tubular section (54) to pivot away from the needle (16) before use of the needle, and which, after use of the needle and the pivoting back of the second tubular section (54) to its first position, is positionable by applying force thereto to grip the pointed end of the needle (16) to lock the needle point within the movable element (19) and the second tubular section (54) of the safety package in its first position.

17 Claims, 1 Drawing Sheet

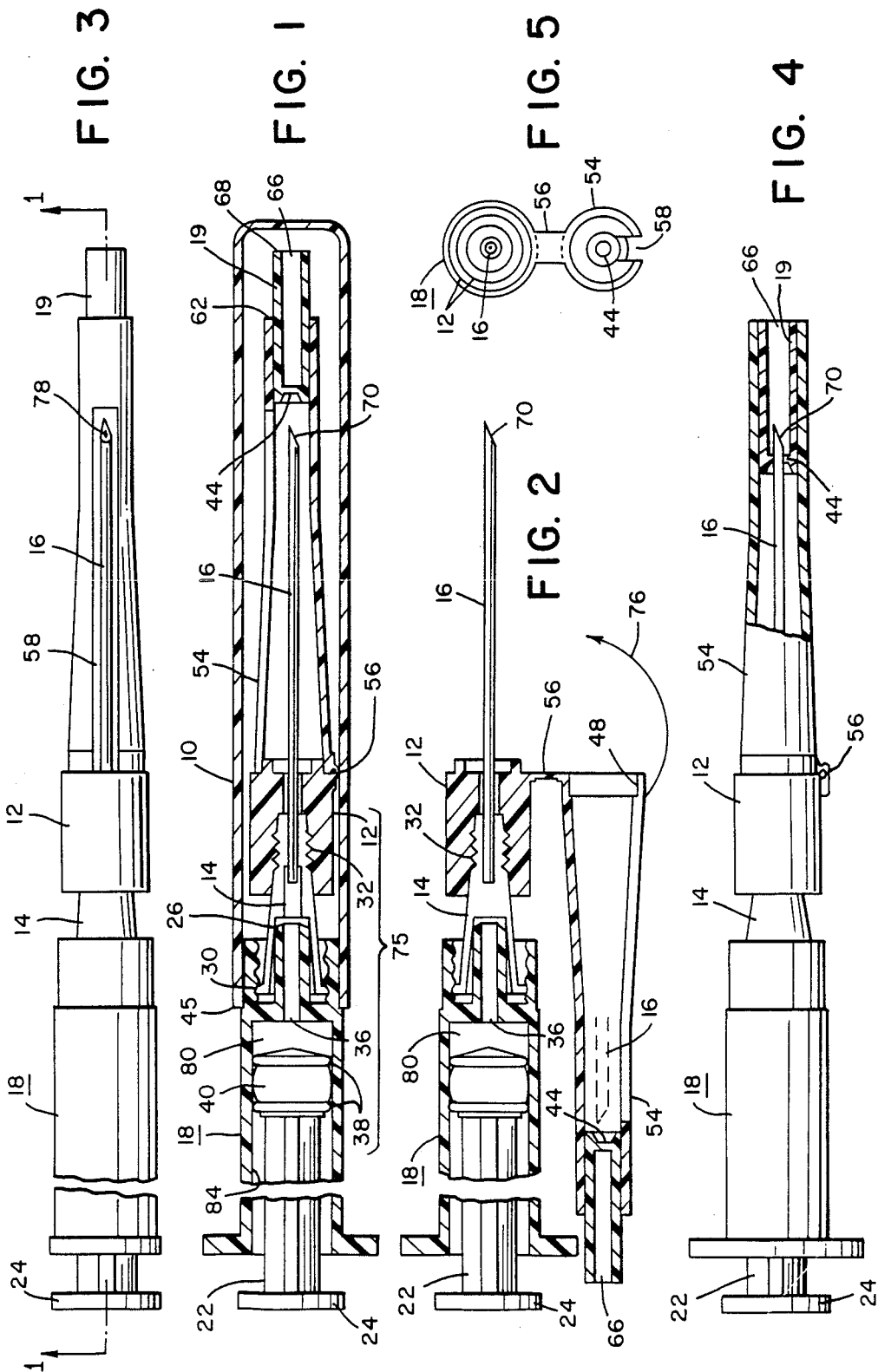

SAFETY PACKAGING FOR HYPODERMIC SYRINGES WITH NEEDLES AND THE LIKE

This invention relates generally to the packaging of the hypodermic syringe including its bored out needle, or a cannula type needle, which is a needle with a catheter extending through a bore in the needle, for entering the catheter into the patient's vein, and more particularly to a safety packaging for such devices to prevent accidental pricking of a person by the pointed end of the needle during shipping and up to the point of use and then, immediately after such use, protectively covering the needle and especially its point permanently so that it cannot accidentally prick someone and can be disposed of safely.

In this specification the term needle or hypodermic needle is to be interpreted to also include the cannula type needle with the bore therein for a catheter to be inserted into the patient's vein. There are in the prior art several packaging devices designed to protect the user, such as a nurse, a medical technician, or any other person who might come in contact with the needle, either used or unused, from being pricked accidentally by the needle and thereby possibly becoming infected with some disease. The need for safe packaging of hypodermic needles with or without the syringe with which they are used has become considerably more acute since the appearance of a recently identified new deadly disease called Acquired Immune Deficiency or AIDS and which is now rapidly spreading throughout most of the world and in almost all cases proving to be fatal. AIDS is thought to be transmitted in a number of ways including blood to blood contact of an AIDS victim with the blood of an uninfected person, as by means of a contaminated hypodermic needle. Since many people can carry the AIDS virus for long periods of time extending into several years without showing symptoms, it frequently occurs that they are given inoculations for one reason or another, or give blood, with the needle used therefor becoming contaminated with the AIDS virus and, if used again on a non-infected person, can infect such non-infected person with AIDS, and possibly other diseases.

As a result of the AIDS crisis, there has arisen a strong demand for the safe packaging of hypodermic needles from the time they are manufactured to the time of their first use and then, immediately after such first use, the packaging must be constructed so that it can be closed over the needle, especially the tip thereof so that no person can be pricked by the needle, and with the needle locked therein in a substantially permanent manner. The needle, or the entire hypodermic syringe including the needle, can then be disposed of without danger of pricking any person handling the hypodermic syringe and needle after use thereof, short of deliberately tearing the protective packaging off the needle for illegal use thereof.

There are in the prior art several devices which are packaged to protect both the nurse or any other person from being accidentally pricked by the needle before use since the external packaging is not removed until immediately before use of the needle. External packaging which protects the sharp end of the needle from being exposed until use is shown in several issued U.S. patents including U.S. Pat. No. 2,854,976 issued Aug. 7, 1958 to Heydrich and entitled "Protective Device for Needles of Hypodermic Syringes" and U.S. Pat. No. 3,537,452 issued Nov. 3, 1970 to Wilke and entitled "Needle Cover and Bevel Guard".

Other hypodermic needle packaging devices employ a needle guard which is hingedly connected to the needle hub by suitable means and has a longitudinal groove formed therein through which the needle can pass as the needle guard is pivoted away from the needle on the hinge. A resilient hook (biased in a first direction by the needle before use) is formed on the back wall of the needle guard. When the needle guard is pivoted back to its original position to encase the needle, the now unbiased hook and the needle are manually pressed against each other in such a manner that the needle is forced back of the hook simply by applying sufficient pressure to the needle guard housing as it is pivoted back to encase the needle. More specifically, as the needle guard covers the needle, the needle is forced against the resilient hook, moving the hook to one side (in a second direction) and then snapping in back of the hook. In other words the needle passes the end of the hook by virtue of the applied force between the hook and the needle so that the hook is forced aside allowing the needle to move past the end of the hook which then captures the needle behind the hook. An example of this type prior art is shown in U.S. Pat. No. 4,664,259 issued May 12, 1987 to Landis and entitled "Needle Container and Method for Preventing Accidental Contact With a Needle".

In still another form of the prior art the needle guard is completely removed from the rest of the assembly including the syringe, the needle, and the needle hub, in a direction transverse to the needle. More specifically, the needle protector has a base portion which forms a partial cylinder with an opening slot therein whose width is somewhat less than the width of the needle hub and simply snaps over the needle hub when the nurse or medical technician applies pressure thereto. In the same manner the needle protector can be removed to expose the needle for use. This type structure is illustrated in U.S. Pat. No. 4,643,722 issued 2/17/87 to Smith and entitled "Closure System for Storage, Transport and Exposure of Hypodermic Needles". Here again the needle protector only functions to provide adequate protection up until the time of usage. In the above cited Smith prior art patent the needle protector is completely removed from the remainder of the assembly and can be misplaced or simply failed to be snapped back on the main assembly to protect the needle. The risk of accidentally pricking someone, or of deliberate reuse of the contaminated needle in this type structure is obviously relatively high compared to other needle protective devices.

A primary object of the invention is to provide an improved safe packaging for the needle from the time of manufacture continuously up to the time of usage and then, immediately after usage, until the time of final, irretrievable disposal of the entire assembly with minimal risk to anyone either accidentally or deliberately re-exposing the contaminated needle and pricking someone.

A second object of the invention is to provide a safe package for a hypodermic syringe needle or a cannula type needle which employs a pivotal needle guard housing with a longitudinal slot therein and which can be pivoted away from the needle by hinge means to expose the needle immediately before use and then, immediately after use, be pivoted back to encase the needle, and having a movable element encased in an extension of the pivotal needle guard beyond the needle's pointed end which can be employed to lock the needle permanently within the needle guard after usage so that not only is the point of the needle covered and fully protected from accidentally pricking someone but also the pivotal housing is permanently locked in a position surrounding the needle by virtue of the movable element which is now secured to the needle and which is positioned within the pivotal housing portion of the needle guard.

A third object of the invention is to sterilize the end of the needle after usage thereof by the same movable element which locks the needle and needle guard after usage of the needle in a position to prevent accidental pricking of someone by the needle.

A fourth object of the invention is to provide an improved and inexpensive safety package for a hypodermic needle which protects the needle from pricking someone at all times except during the short period of time the nurse is using the needle on a patient.

In accordance with a preferred form of the invention there is provided a safety package for preventing unwanted skin pricking of a person by a hypodermic needle or a cannula type needle mounted on a needle hub and comprising a hinge, first and second sections of a needle guard having longitudinal bores therethrough and connected together at their first ends by the hinge with the first section substantially irremovably connected to the needle hub and the second section surrounding the needle and having an elongated slot therein positioned to enable the needle to pass therethrough when the second section of the needle guard is pivoted away from the needle by means of the hinge. The second end of the second section of the safety package beyond the end of the needle by a predetermined distance and contains a movable element substantially permanently connectable to said needle after usage thereof to prevent the second section of the needle guard from moving relative to the needle and therefore to prevent exposure of the needle to any person after usage of the needle.

In accordance with a more specific form of the invention, the movable element contained in the extended portion of the second portion of the needle guard can be frictionally held therein with a portion of the movable element extending outwardly from the open end of the second section of the needle guard and, after the second section of the needle guard is pivoted back to enclose the needle, the nurse or technician can simply press the end of the movable element on a flat surface, such as the top of a desk, which will force the movable element into the point of the needle a sufficient distance such that the end of the movable element is substantially flush with the end of the second section of the needle guard and could be removed only with great difficulty. Thus, the point of the needle is embedded in the movable element, thereby not only protecting the end of the needle from exposure but also locking the second section of the needle guard securely in position to enclose the needle.

In one feature of the invention the movable element contained in the extended portion of the needle protector can be treated with a germicide so that in the remote event someone accidentally or deliberately obtains possession of such contaminated needle and destroys the safety package along with the movable element to expose the needle for illicit use or any other use would, in effect, be using a sterilized needle. An external sealing device can be employed to hermetically seal the entire structure until use thereof.

The above-mentioned and other objects and features of the invention will be more fully understood when read in conjunction with the drawings in which:

FIG. 1 shows an axial oriented sectional view of the hypodermic syringe, the needle and the protective safety package as it is delivered from the manufacturer and before the nurse or medical technician has removed either the external sealing device or has pivoted the upper part of the needle protector away from the needle to expose the needle for use, as is shown in FIG. 2;

FIG. 2 shows another axially oriented sectional view of the invention with the upper portion of the needle guard pivoted back and away from the needle to expose the needle for use by a nurse or medical technician;

FIG. 3 is a side view of the needle of FIG. 2 and clearly shows the slot through which the needle must pass in order to allow the upper portion of the needle guard to be pivoted into the position shown in FIG. 2 wherein the needle is exposed for use;

FIG. 4 shows the needle guard after use of the needle and with the second section of the needle guard pivoted back to its original position to encase the needle and with the movable element in the extended portion of the second section of the needle guard pressed into the end of the needle to lock it within the second section of the needle guard; and FIG. 5 is an end view of the structure of FIG. 2.

Referring now to FIG. 1 the hypodermic needle 16, its hub 14, the syringe 18, and the packaging are shown as they come from the manufacturer. The packaging consists of an outer tubular element 10 closed at one end 11 and with its other, open end 45 slidable engaged over the end of the syringe 18 to completely seal the entire assembly. The safety package includes a two section needle guard consisting of a first base section 12 which can be either permanently secured, or removable secured, to the needle hub 14 by threaded junction 32. The needle hub 14 in turn is secured to the end of the syringe 18 by the threaded connection 30, commonly known as a Leur connection.

A second portion of the needle guard comprises the slightly tapered, elongated cylindrically shaped element 54 which is connected to the base portion 12 of the needle guard by a suitable hinge means 56, which can be of plastic, and surrounds the needle 16 except for the elongated slot 58 which is formed in the second portion 54 of the needle guard and shown only in FIG. 3. As will be discussed later herein the tapered element 54 is pivotal around hinge 56 so that the needle 16 will pass through the elongated slot 58 (FIG. 3) therein as element 54 is pivoted away from needle 16 on a hinge 56 and will be exposed for use as shown in FIG. 2.

As mentioned above the second section 54 of the two section needle guard consists of a slightly tapered cylindrical element 54 with the slot 58 formed therein and having a slightly tapered bore 60 therethrough which preferably becomes a true cylindrical bore 64 near the open end 62 thereof. Positioned within the bore 64 formed by the end of the tapered cylinder 54 is a frictionally held element 19 which also preferably has a tapered bore 66 therein extending from the end 68 thereof to the membrane 44 therein. It can be seen that the inner bore 66 of element 19 is axially aligned with the needle 16 and when element 19 is pushed towards the pointed end 70 of needle 16, as by pressing the end of the element 19 on a hard surface such as a desk top, the point of the needle 16 will forcibly penetrate the membrane 44 and will be locked within the element 19.

It should be noted that the element 19 should be pushed into the needle guard section 54 until the end 68 of element 19 is flush with the end 68 of needle guard section 54 to make removal of element 19 from needle guard section 54 extremely difficult. In the pressed-in position of element 19 it is apparent that needle 16 is fully protected in that it is virtually impossible for anyone to become pricked by the end 70 of needle 16.

The external sealing device 10, which can resemble a test tube, fits sufficiently snugly over the cylindrical end of the syringe 18 to hermetically seal the entire structure including cylindrical position 54 of the needle guard, the base 12 of the needle guard, and the needle hub 14. Such external sealing device 10 is removed by the nurse immediately before use of the needle to maintain the needle 16 in a sterile condition until used.

The precise means by which the tapered needle guard section 54 is pivoted away from the needle 16 to expose the needle for use will be more clearly seen from the following discussion of FIG. 2 along with details of the needle guard base 12, the needle hub 14, and a suitable manner by which they can be secured to each other and to the syringe 18.

The needle 16 extends from its point 70 back through the base 12 of the needle guard and the needle hub 14, which are identified together generally by reference character 75. If desired, the needle hub 14 can be an integral and permanent part of the base 12 of the needle guard and identified by the reference character 75. Alternatively, the needle hub 14 can be separate from the base portion 12 of the needle guard by suitable means such as threaded joint 32 which secures the interior of the left end of base section 12 of the needle guard to the exterior of the right end of the needle hub 14. Other suitable means of securing the base of the needle guard to the needle hub 14 will be obvious to those of ordinary skill in the art. The needle hub 14 in turn is secured to the right end of syringe 18 by the conventional Leur means (thread junction 30), or any other suitable means.

As indicated above, FIG. 2 shows the structure of FIG. 1 with the external sealing device 10 removed therefrom and with the upper portion 54 of the needle guard pivoted away from needle 16 into a position to allow full exposure of needle 16 for use.

The second section 54 of the needle guard is pivoted away from the base 12 of the needle guard by means of hinge 56 which can be a simple flexible plastic connection between the upper (54) and lower (12) sections of the needle guard. The direction of pivoting of the upper section 54 of the needle guard is shown by the curved arrow 76 in FIG. 2. It is apparent that the needle 16 is required to pass through the slot 58 (FIG. 3) in the side of the second section 54 of the needle guard. The slot 58 is shown clearly in FIG. 3 which is a side view of the upper section 54 of the needle guard. It will be noted again in FIG. 2 that the needle 16 extends through the base 12 of the needle guard and the needle hub 14, which can be formed as a single unit 75 by removing the threaded junction 32.

The needle 16 has a bored out interior 78 (FIG. 3) to allow flow of fluid, such as blood, nourishment, or medication, etc., in either direction between the patient and the syringe 18 (FIG. 1) depending upon the need. That end of the needle 16 extending through the needle hub 14 and the base section 12 of the needle guard extends into the cavity 80 of the syringe 18. It will be seen in both FIGS. 1 and 2 that the syringe 18 is attached to a combination of the needle hub 14 and the base section 12 of the needle guard by means of the threaded junction 30 between the right end of syringe 18 and the left end of needle hub 14.

The conventional syringe 18 includes, in addition to its basic container cavity 80, an internal plunger 40 which is attached to an arm 22 which in turn extends through the left end of syringe 18 and terminates in a suitable handle 24 which the nurse can move towards or away from the body of the syringe to move the plunger 40 back and forth within the syringe so as to draw fluid such as blood into the syringe cavity 80 or force fluid from the syringe cavity 80 into the patient's vein through the bore 78 in the needle 16 once the needle 16 has been inserted into the patient's vein.

The plunger disc 40 is of a resilient and durable material such as a resilient plastic and has, around the perimeter thereof, an annular ring 38, which presses against the inner surface 84 of cylinder 86.

The end 88 of the syringe 18 can be permanently affixed thereto and has a small aperture 36 in the center thereof with an annular, resilient element 26 formed around the orifice 36 through which the non-pointed end of needle 16 is inserted to connect cavity 80 to the bore in needle 16. The annular element 26 fits snugly around the needle 16, thereby forming a good seal between the needle 16 and the walls of orifice 36.

If desired, element 26 can be made of a material which is sufficiently resilient so that orifice 36 will close completely in the absence of the needle being inserted therethrough but when a needle is inserted therethrough the orifice 36 will expand to receive the needle to insure a good seal between needle 16 and orifice 36 as well as forming a good support for needle 16.

The connection between the needle hub 14 and the syringe 18 is such that the syringe can be completely removed from the needle by means of the Leur connection 30, leaving the needle 16 in the patient's arm. A new syringe can then be secured on the end of the needle hub 14 in cases where more than one syringe of blood is to be removed from the patient or more than one syringe of solution is to be injected into the patient's vein.

As mentioned above FIG. 2 shows the assembly of the upper portion 54 of the needle guard pivoted downwardly in the direction of the arrow 76 by means of hinge 56 so that the needle 16 is fully exposed for use. The needle 16 is, shown only in dashed line form in the pivoted away upper portion 54 of FIG. 2 since the upper portion 54 of the needle guard has, in fact, been pivoted away from needle 16, leaving needle 16 exposed in a horizontal direction as shown in FIG. 2.

As indicated above, FIG. 3 is a side view of FIG. 1 and shows the slot 58 through which the needle 16 passes when the upper portion 54 of the needle guard is pivoted away from its base portion 12, as shown in FIG. 2.

The safety packaging structure of the present invention can also be employed with an intravenous (IV) arrangement (not shown) whereby a container of fluid is suspended above the patient with means for controlling the rate of flow of the fluid through a catheter and into the patient's vein.

The catheter normally is inserted into the patient's vein by a cannula type needle which has the catheter extending through a bore in the needle. After the catheter is securely in place in the patient's vein the needle is carefully withdrawn and the catheter taped to the patient's body (usually the wrist) to secure the position of the catheter in the patient's vein.

The cannula type needle and the catheter can be packaged as shown in FIG. 1, but without the syringe 18. A tube leading to the suspended container can be connected to the left end of the needle hub 14 by the Leur connection 30. If desired, the base 12 of the needle guard can be from the catheter in an IV application by forming the longitudinal slot formed therein along its entire length, including the needle guard base, (not shown in the figures). The base 12 of the needle guard can then be unscrewed from threaded junction 32 and removed from the needle 16 and the catheter through the slot (not shown) in base 12 of the needle guard. The hinge 56 can be severed before removing the base 12.

After completion of the use of the cannula type needle a structure such as a new needle guard can be screwed onto the needle hub of the cannula type needle and the element 19 pressed into the point of the needle as discussed above.

While the drawings show the invention to be made entirely of plastic, except for the needle 16, which is a steel alloy in most cases, and the plunger 40, which can be of rubber, plastic, or other suitable material, the syringe and the package, or portions thereof can be made of materials other than plastics, such as various metals for example. Also, the sectional configuration of the needle guard and the element 19 can have a shape other than circular, such as square, rectangular, oval, or any other suitable configuration. Nor is the tapered configurations of needle guard element 54 or the bores of needle guard 54 on element 19 necessary. They can be of true cylindrical shape or of other suitable shapes. Further, the element 19 can be of any configuration that will permanently trap the end of needle 16 when pushed into needle 16. For example, the membrane 32 can be positioned beyond the tip of needle 16 when pushed into the extension of needle guard 54 with the bore 66 having a smaller diameter, but larger than the diameter of needle 16. In this last mentioned configuration, the tip of the needle cannot be reached from the end 68 of element 19.

It is to be understood that the forms of the invention shown and described herein are but preferred forms thereof and other forms and modification of the invention may occur to others of ordinary skill in the art without departing from the spirit or scope of the appended claims.

I claim:

1. A needle guard package for protecting persons from accidental pricking by a hypodermic type needle having a first end secured within a needle hub and comprising;
    a first generally tubular section of said needle guard package securable to and surrounding at least a portion of said needle hub;
    a second generally tubular section of said needle guard package having an elongated slot formed therein;
    a hinge connecting together said first and second sections of said needle guard package;
    said second section of said needle guard package positioned in a first position around said needle so that when said second section is pivoted away from said needle on said hinge said needle passes through said longitudinal slot to expose the point of said needle for use;
    said second section having the end thereof opposite its hinged end extending beyond the needle point; and
    a plastic insert frictionally held within the extended end of said second section a predetermined distance from the needle point and movable into the said needle point to lock said needle permanently therein after use of said needle and after said second section has been moved into its first position surrounding said needle.

2. A needle guard package as in claim 1 in which said plastic insert is impregnated with a germicide for destroying bacteria and/or viruses detrimental to the health of a mammal.

3. A safety package for the needle in a hypodermic syringe having a needle hub joining a first end of the needle to the syringe or a cannula type needle secured to a hub and comprising:
    a hinge secured to said needle hub;
    a tubular section having a longitudinal slot formed therein and secured at a first end to said needle hub by said hinge and surrounding said needle in a first position to pivot about said hinge and away from said needle to a second position with said needle passing through said longitudinal slot to expose the second, pointed end of said needle for use and, after use of said needle, to pivot said tubular section back to its first position;
    said tubular section having its second end extending beyond the point of the needle and containing a movable, piercable element therein which is positioned beyond the end of the needle point before use of the needle and which, after use of said needle and the pivoting back of said second section to its first position, is pushed against the needle point to cause said needle point to penetrate said piercable element, thereby locking the needle point within said piercable element and said tubular section of said safety package around said needle.

4. A safety package as in claim 3 in which said movable piercable element is impregnated with a germicide for destroying organisms detrimental to the health of a human being.

5. A safety package for preventing accidental skin pricking by the needle in a hypodermic syringe having a needle hub joining the needle to the syringe or a cannula type needle secured to a needle hub and comprising:
    a first section securable at its first end to said needle hub;
    a hinge secured to the second end of said first section;
    a second section secured at a first end to said hinge and surrounding said needle in a first position with a longitudinal slot formed therein and positioned to pivot about said hinge and away from said needle to a second position with said needle passing through said longitudinal slot to expose said needle for use and, after use of said needle, to pivot said second section back to its first position;
    said second section having its second and extending beyond the needle point and containing therein a non-attached, movable element therein which is positioned to allow said second section to swing away before use of said needle, and which, after use of said needle and the pivoting back of said second section to its first position, is positionable by applying force to said movable element to grip the pointed end of said needle to thereby lock said needle point within said movable element and said second section of said safety package in its first position.

6. A safety package as in claim 5 in which said movable element is impregnated with a germicide for destroying organisms detrimental to the health of a mammal.

7. A safety package for preventing accidental pricking by the pointed end of the needle of a hypodermic syringe having a needle hub joining the needle to the syringe or a cannula type needle secured to a needle hub and comprising:
   a hinge pivotally connecting said needle hub to a first end of said safety package;
   a first tubular section surrounding said needle in a first position with a longitudinal slot formed therein and positioned to pivot about said hinge and away from said needle to a second position with said needle passing through said longitudinal slot to expose said needle for use and, after use of said needle, to pivot said first tubular section back to its first position; and
   a second tubular section connected axially to said first tubular section and extending beyond the pointed end of said needle and containing a movable element therein which is positioned beyond the sharp end of said needle before use of said needle and which, after use of said needle and the pivoting back of said second section to its first position, is pushed against the sharp needle end to engage the pointed end of said sharp needle end to lock said pointed end of said needle substantially permanently within said movable element and further to lock said first tubular section substantially permanently around said needle.

8. A safety package as in claim 7 in which said movable element is impregnated with a germicide for destroying bacteria and/or viruses detrimental to the health of a human being.

9. A safety package for preventing unwanted skin pricking by a needle or a cannula type needle mounted on a needle hub and comprising:
   a hinge;
   first and second sections having longitudinal bores therethrough connected together at their first ends by said hinge with said first section substantially irremovably connected to said needle hub and said second section surrounding said needle and having an elongated slot therein positioned to enable said needle to pass therethrough for use when said second section is pivoted away from said needle on said hinge; and
   with the second end of said second section extending beyond the end of said needle a predetermined distance and containing an element substantially permanently connectable to said needle to prevent said needle from moving relative to said second section and therefore to prevent exposure of said needle.

10. A safety package as in claim 9 in which said element is impregnated with a germicide for destroying bacteria and/or viruses detrimental to the health of a human being.

11. A safety package for the needle in a hypodermic syringe having a needle hub joining a first end of the needle to the syringe and comprising:
    a first tubular section securable at its first end to said needle hub;
    a hinge secured to the second end of said first section;
    a second tubular section having a longitudinal slot formed therein and secured at a first end to said hinge and surrounding said needle in a first position to pivot about said hinge and away from said needle to a second position with said needle passing through said longitudinal slot to expose said needle for use and, after use of said needle, to pivot said second section back to its first position;
    said second tubular section having its second end extending beyond the point of the needle and containing a movable element therein which is positioned beyond the end of the needle point before use of the needle and which, after use of said needle and the pivoting back of said second tubular section to its first position, is pushed against the needle point to cause said needle point to substantially permanently engage said movable element, thereby locking the needle point within said movable element and said second tubular section of said safety package around said needle.

12. A method for preventing unwanted skin pricking by a hypodermic needle or a cannula type needle mounted on a needle hub comprising the steps of:
    providing first and second sections having longitudinal bores therethrough connected together at their first ends by a hinge with said first section substantially irremovably connected to said needle hub and with said second section surrounding said needle;
    forming an elongated slot in said second section positioned to enable said needle to pass therethrough when said second section is pivoted away from said needle on said hinge;
    extending said second section beyond the sharp end of said needle a predetermined distance and containing a movable element extending out of the end of said second section and substantially permanently connectable to said needle; and
    moving said movable element into the sharp end of said needle to prevent said needle from moving relative to said second section and therefore to prevent exposure of said needle outside of said second section.

13. A method as in claim 12 comprising the further step of impregnating the movable element with a germicide/antibiotic solution to destroy bacteria or viruses injurious to the health of a human being.

14. In a hypodermic syringe having a needle hub joining a bored needle to the syringe or a cannula type needle secured to a hub, a method for preventing accidental pricking of a person by the sharp first end of the needle and comprising:
    securing a first section of a safety package at its first end to the second end of the needle with the major portion of the needle extending therefrom;
    securing a first side of a hinge to the second end of said first section;
    securing a first end of a second section of the safety package which has a longitudinal slot formed therein to a second side of said hinge and which, in a first position, surrounds said needle and is pivotal about said hinge and away from said needle to a second position with said needle passing through said longitudinal slot to expose said needle for use and, after use of said needle, to pivot said second section back to its first position to again surround said needle;

extending the second end of said second section beyond the sharp end of said needle;

providing a movable and piercable element in the extended portion of said second section beyond the sharp end of the needle before use of the needle;

pivoting back said second section to its first position after use of said needle; and pushing said piercable element against the sharp end of said needle to cause said sharp needle end to penetrate said piercable element, thereby locking said sharp needle end within said piercable element and said second section of said safety package around said needle.

15. A method as in claim 14 comprising the further step of impregnating the piercable movable element with a germicide/antibiotic solution to destroy bacteria or viruses injurious to the health of a human being.

16. A method for preventing unwanted skin pricking by a hypodermic type needle mounted on a needle hub comprising the steps of:

providing first and second tubular sections having longitudinal bores therethrough and connected together at their first ends by a hinge;

connecting said first tubular section together at their first ends substantially irremovably to said needle hub with said second tubular section surrounding said needle;

forming an elongated slot in said second tubular section positioned to enable said needle to pass therethrough when said second tubular section is pivoted away from said needle on said hinge to enable use of said needle;

extending said second tubular section beyond the sharp end of said needle by a predetermined distance;

providing a movable element positioned beyond the end of said sharp needle point before use thereof and extending into the extended end of said second tubular section; and engaging said movable element with the sharp end of said needle to prevent said needle from moving relative to the surrounding second tubular section and therefore to prevent exposure of said needle outside of said second tubular section.

17. A method as in claim 16 comprising the further step of impregnating the movable element with a germicide/antibiotic solution to destroy bacteria or viruses injurious to the health of a human being.

* * * * *